(12) United States Patent
Enomoto

(10) Patent No.: US 8,378,309 B2
(45) Date of Patent: Feb. 19, 2013

(54) RADIATION DETECTOR, RADIOGRAPHIC IMAGE CAPTURING SYSTEM, RADIATION DETECTION METHOD, RADIATION DETECTION PROGRAM STORAGE MEDIUM, AND CONTROLLER

(75) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/267,886

(22) Filed: Oct. 7, 2011

(65) Prior Publication Data

US 2012/0091353 A1 Apr. 19, 2012

(30) Foreign Application Priority Data

Oct. 19, 2010 (JP) ................................. 2010-234579

(51) Int. Cl.
*G01T 1/24* (2006.01)
(52) U.S. Cl. ................................. 250/370.08; 250/370.09
(58) Field of Classification Search .............. 250/370.08
See application file for complete search history.

(56) References Cited

U.S. PATENT DOCUMENTS

2002/0181654 A1* 12/2002 Baertsch et al. ............. 378/98.8
2003/0194058 A1* 10/2003 Tsujii ............................ 378/210

FOREIGN PATENT DOCUMENTS

| JP | 2003-307569 A | 10/2003 |
|---|---|---|
| JP | 2004065635 | 3/2004 |
| JP | 2005-013272 A | 1/2005 |
| JP | 2005351879 A * | 12/2005 |
| JP | 2008132216 | 6/2008 |
| JP | 2010214056 | 9/2010 |

OTHER PUBLICATIONS

Partial English launguage translation of the following; Office action dated Oct. 23, 2012 from the Japanese Patent Office in a Japanese patent application corresponding to the instant patent application. This office action translation is submitted now in order to supplement the understanding of patent document JP 2008-132216, JP2004-065635 and JP2010-214056 which are cited in the office action and are being disclosed in the instant Information Disclosure Statement.

* cited by examiner

*Primary Examiner* — Marcus Taningco
(74) *Attorney, Agent, or Firm* — SOLARIS Intellectual Property Group, PLLC

(57) ABSTRACT

A radiation detector includes a detection unit, a detection control unit, an image analyzing unit and a determination unit. The detection unit detects radiographic image data by plural pixels that convert applied radiation into electrical signals and store the electrical signals. The detection control unit controls the detection unit so as to determine that radiation has been applied if a read value obtained by reading the electric signals stored in the plural pixels is equal to or greater than a threshold value, and acquire radiographic image data corresponding to radiation that has passed through a subject. The image analyzing unit performs an image analysis with respect to the radiographic image if the read value is equal to or greater than the threshold value. The determination unit determines based on the result of the image analysis whether or not the radiographic image has been detected at an intended timing.

15 Claims, 6 Drawing Sheets

RADIATION DETECTOR, RADIOGRAPHIC IMAGE CAPTURING SYSTEM, RADIATION DETECTION METHOD, RADIATION DETECTION PROGRAM STORAGE MEDIUM, AND CONTROLLER

CROSS-REFERENCE TO RELATED APPLICATION

This application claims priority under 35 USC 119 from Japanese Patent Application No. 2010-234579 filed on Oct. 19, 2010, the disclosure of which is incorporated by reference herein.

BACKGROUND OF THE INVENTION

1. Field of the Invention

The present invention pertains to a radiation detector, a radiographic image capturing system, a radiation detection method, a radiation detection program storage medium, and a controller and particularly relates to a radiation detector, a radiographic image capturing system, a radiation detection method, a radiation detection program storage medium, and a controller that capture a radiographic image without having to synchronize with a radiation application action of a radiation applicator.

2. Description of the Related Art

Conventionally, radiographic image capturing systems that perform radiographic imaging for the purpose of medical diagnoses have been known. As one such radiographic image capturing system, there is a radiographic image capturing system that is equipped with a radiation applicator that applies radiation, a radiation detector—such as what is known as a cassette—that detects the radiation that has passed through a subject to capture a radiographic image, and a controller that controls the radiation applicator and the radiation detector.

In recent years, there have been radiation detectors using a flat panel detector (FPD) that is capable of converting the detected radiation into electrical signals. Because dark current, which contributes to noise, exists in a two-dimensional solid-state imaging device such as an FPD, the imaging time of the solid-state imaging device cannot be lengthened unreasonably. For this reason, synchronization of the application action, in which the radiation detector transmits signals to and receives signals from the radiation applicator and in which the radiation applicator applies the radiation, and the imaging action, in which the FPD performs imaging (performs detection of the radiation), is performed.

Specifically, with respect to an imaging request signal from the radiation applicator, the FPD performs initialization of the solid-state imaging device and, after the initialization has been completed, transmits an imaging preparation completion signal to the radiation applicator. After the radiation applicator receives the imaging preparation completion signal, the radiation applicator starts the application of the radiation, ends the application of the radiation after a preset application time has elapsed, and transmits an application end signal to the FPD. When the FPD receives the application end signal, the FPD ends a charge storage action by the solid-state imaging device and transitions to an output action in which the FPD outputs image data of the detected radiographic image to the controller.

In such cases as this, since the radiation applicator is hand-operated in order to control the FPD, the interface for an operator becomes complex and it is necessary to configure the radiation applicator and the FPD as a single integrated system. This leads to an increase in the size and an increase in the complexity of the device.

As a radiation detector that addresses such problems, there is a radiation detector in which the radiographic image is detected by the radiation detector without having to connect to the radiation applicator and without having to transmit signals to and receive signals from the radiation applicator (without having to synchronize with the radiation applicator). For example, Japanese Patent Application Laid-Open (JP-A) Nos. 2005-13272 and 2003-307569 disclose technologies in which the timing of the application of the radiation is determined by the FPD.

A radiation detector has been proposed that determines an application timing, which is the timing of the application of the radiation that is applied from the radiation applicator in order to capture a radiographic image of a subject, when charge information (electrical signals) that has been read out from the solid-state imaging device has reached a predetermined threshold value or greater.

In this radiation detector, there are cases in which the radiation detector may capture a radiographic image (detect image data) at a wrong timing that is originally not a correct (intended) timing when the radiation detector is to capture a radiographic image of the subject.

It is known that there are cases in which, for example, as a result of the radiation detector being dropped or the like and given an impact, electrical signals are generated just as if radiation had been applied. If the electric signals are equal to or greater than the predetermined threshold value, a radiographic image is captured even though it is not a correct timing when the radiation detector is to capture a radiographic image. The radiographic image that has been captured at an unintended timing in this way is an unintended radiographic image that is not a correct (intended) radiographic image. However, because it cannot be judged whether the radiographic image has been captured at an intended timing or has been captured at an unintended timing, the user can misunderstand that the imaging has ended by obtaining the unintended radiographic image. In cases such as this, the user may need to register the imaging menu (imaging conditions for capturing the subject, etc.) again for a retake.

The present invention provides a radiation detector, a radiographic image capturing system, a radiation detection method, a radiation detection program storage medium, and a controller that can determine whether or not a radiographic image is an image that has been detected at a correct (intended) timing.

SUMMARY

A first aspect of the present invention is a radiation detector including: a detection unit that detects image data of a radiographic image by plural pixels that convert applied radiation into electrical signals and store the electrical signals; a detection control unit that controls the detection unit so as to determine that radiation has been applied if a read value obtained by reading the electric signals stored in the plural pixels is equal to or greater than a threshold value and acquire image data of a radiographic image corresponding to radiation that has passed through a subject; an image analyzing unit that performs an image analysis with respect to the radiographic image based on the detected image data if the read value is equal to or greater than the threshold value; and a determination unit that determines on the basis of the result of the image analysis whether or not the radiographic image is an image that has been detected at an intended timing.

The image analyzing unit performs the image analysis with respect to the radiographic image based on the image data that have been detected by the detection unit if the read value obtained by reading the electrical signals stored in the pixels is equal to or greater than the threshold value. The determination unit determines on the basis of the result of the image analysis by the image analyzing unit whether or not the radiographic image is an image that has been detected at a correct (intended) timing.

There are cases in which the radiation detector detects a radiographic image at an unintended timing that is not an intended timing. For example, if the radiation detector being dropped or given a shock, a radiographic image is captured even though it is not a timing when the radiation detector is to capture a radiographic image (an intended timing). In the present aspect, the image analyzing unit performs the image analysis with respect to the radiographic image based on the image data that have been detected by the detection unit if the read value obtained by reading the electrical signals stored in the pixels is equal to or greater than the threshold value. Therefore, it can be determined on the basis of the result of the image analysis whether or not the radiographic image is an image that has been detected at an intended timing.

In the present aspect, the radiation detector may further include an output unit that outputs the image data to the outside; and an output control unit that controls the output unit so as to prevent outputting of the image data to the outside if the determination unit has determined that the radiographic image is not an image that has been detected at an intended timing.

According to this configuration, a radiographic image that has been detected at an unintended timing can be prevented from being outputted.

In the present aspect, the image analyzing unit may perform the image analysis using a mean value of pixel values of a predetermined number of pixels of the radiographic image.

In the present aspect, the image analyzing unit may perform the image analysis on the basis of a difference between a mean value of pixel values of a predetermined number of pixels of the radiographic image and a mean value of pixel values of a predetermined number of pixels of a radiographic image that has been detected at an intended timing.

In this way, by configuring the image analyzing unit to perform the image analysis using a mean value of pixel values of a predetermined number of pixels of the radiographic image, processing time for the image analysis can be shortened compared to a case in which, for example, a histogram analysis is performed.

In the present aspect, the predetermined number of pixels may be all pixels of the radiographic image or pixels in a predetermined region of the radiographic image.

By configuring the image analyzing unit to use the predetermined number of pixels in a predetermined region of the radiographic image, processing time for the image analysis can be shortened even more compared to a case in which all pixels are used.

In the present aspect, the detection control unit may control the detection unit in a case in which imaging conditions of a radiographic image of the subject have been registered from the outside.

In a case in which imaging conditions have been registered from the outside, if the radiation detector, in which the detection control unit determines that radiation has been applied and controls the detection unit, outputs to the outside image data of a radiographic image that is not an image that has been detected at an intended timing, the user must register again the imaging conditions for retaking. In such radiation detector, by performing control so as to prevent output to the outside image data of a radiographic image that is not an image that has been detected at an intended timing, the waste of having to re-register the imaging conditions can be eliminated.

A second aspect of the present invention is a radiographic image capturing system including: a controller that instructs imaging conditions relating to capturing a radiographic image; a radiation applicator that applies radiation on the basis of an instruction from the controller; and the radiation detector according to the first aspect, which detects image data of a radiographic image corresponding to the radiation that has been applied from the radiation applicator and outputs the image data to the controller.

A third aspect of the present invention is a radiation detection method including: reading, with a detection unit that detects image data of a radiographic image by plural pixels that convert applied radiation into electrical signals and store the electrical signals, the electrical signals stored in the plural pixels; determining that radiation has been applied if a read value obtained by the reading is equal to or greater than a threshold value and controlling the detection unit so as to acquire image data of a radiographic image corresponding to radiation that has passed through a subject; performing an image analysis with respect to the radiographic image based on the detected image data if the read value is equal to or greater than the threshold value; and determining on the basis of the result of the image analysis whether or not the radiographic image is an image that has been detected at an intended timing.

A fourth aspect of the present invention is non-transitory storage medium storing a program causing a computer to execute radiation detection processing, the radiation detection processing including: reading, with a detection unit that detects image data of a radiographic image by plural pixels that convert applied radiation into electrical signals and store the electrical signals, the electrical signals stored in the plurality of pixels; determining that radiation has been applied if a read value obtained by the reading is equal to or greater than a threshold value and controlling the detection unit so as to acquire image data of a radiographic image corresponding to radiation that has passed through a subject; performing an image analysis with respect to the radiographic image based on the detected image data if the read value is equal to or greater than the threshold value; and determining on the basis of the result of the image analysis whether or not the radiographic image is an image that has been detected at an intended timing.

A fifth aspect of the present invention is a controller including: a receiving unit that receives image data that have been outputted from a radiation detector that reads electric signals from plural pixels that convert applied radiation into electrical signals and store the electrical signals, determines that radiation has been applied if a read value of the electrical signals is equal to or greater than a threshold value, and detects image data; an image analyzing unit that performs an image analysis with respect to the radiographic image based on the received image data; and a determination unit that determines on the basis of the result of the image analysis whether or not the radiographic image is an image that has been detected at an intended timing.

As described above, according to the above-described aspects, it can be determined whether or not a radiographic image is an image that has been detected at an intended timing.

BRIEF DESCRIPTION OF THE DRAWINGS

An exemplary embodiment of the present invention will be described in detail based on the following figures, wherein.

DETAILED DESCRIPTION

Figure 1:
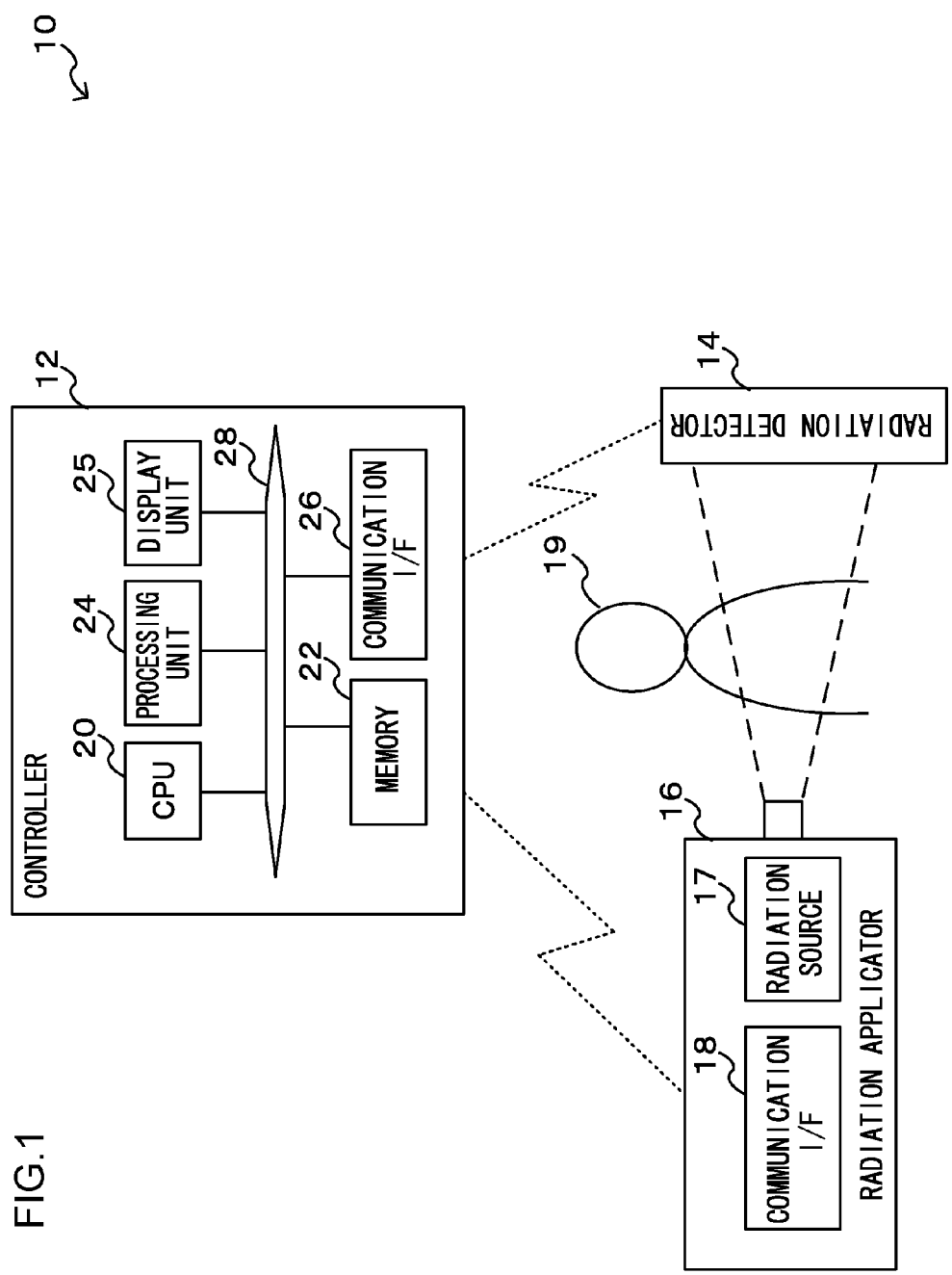
FIG. 1 is a schematic configuration diagram showing an example of the schematic configuration of a radiographic image capturing system pertaining to the exemplary embodiment.

FIG. 1 shows the schematic configuration of a radiographic image capturing system 10 of the present exemplary embodiment. The radiographic image capturing system 10 is equipped with a radiation applicator 16 that applies radiation (e.g., X-rays) to a subject 19, a radiation detector 14 that detects the radiation that has been applied from the radiation applicator 16 and has passed through the subject 19, and a controller (console) 12 that instructs the capture of a radiographic image, acquires image data from the radiation detector 14, and performs various processings. The radiation that carries image information as a result of being applied from the radiation applicator 16 and passing through the subject 19 positioned in an imaging position is applied to the radiation detector 14.

The controller 12 is wirelessly connected to the radiation detector 14 and executes various controls with respect to the radiation detector 14 by wirelessly transmitting commands and data via a communication interface (I/F) 26. The controller 12 is also wirelessly connected to the radiation applicator 16 and controls the timing when the radiation applicator 16 applies the radiation (e.g., X-rays). The controller 12 is equipped with a central processing unit (CPU) 20, a memory 22, a processor 24, a display unit 25, and the communication I/F 26. The CPU 20, the memory 22, the processor 24, the display unit 25, and the communication I/F 26 are interconnected by a bus 28 such as a CPU bus so as to be capable of sending signals to and receiving signals from each other. The CPU 20 controls the actions of the entire controller 12 by executing various programs that are stored beforehand in the memory 22. The processor 24 acquires the image data from the radiation detector 14 and performs various processings. The display unit 25 displays, for example, the radiographic image received via the communication I/F 26 from the radiation detector 14.

The radiation applicator 16 is equipped with a radiation source 17 and a communication interface (I/F) 18. The radiation applicator 16 is wirelessly connected to the controller 12 via the communication I/F 18 and applies the radiation from the radiation source 17 to the subject 19 at a timing based on the control of the controller 12.

Figure 2:
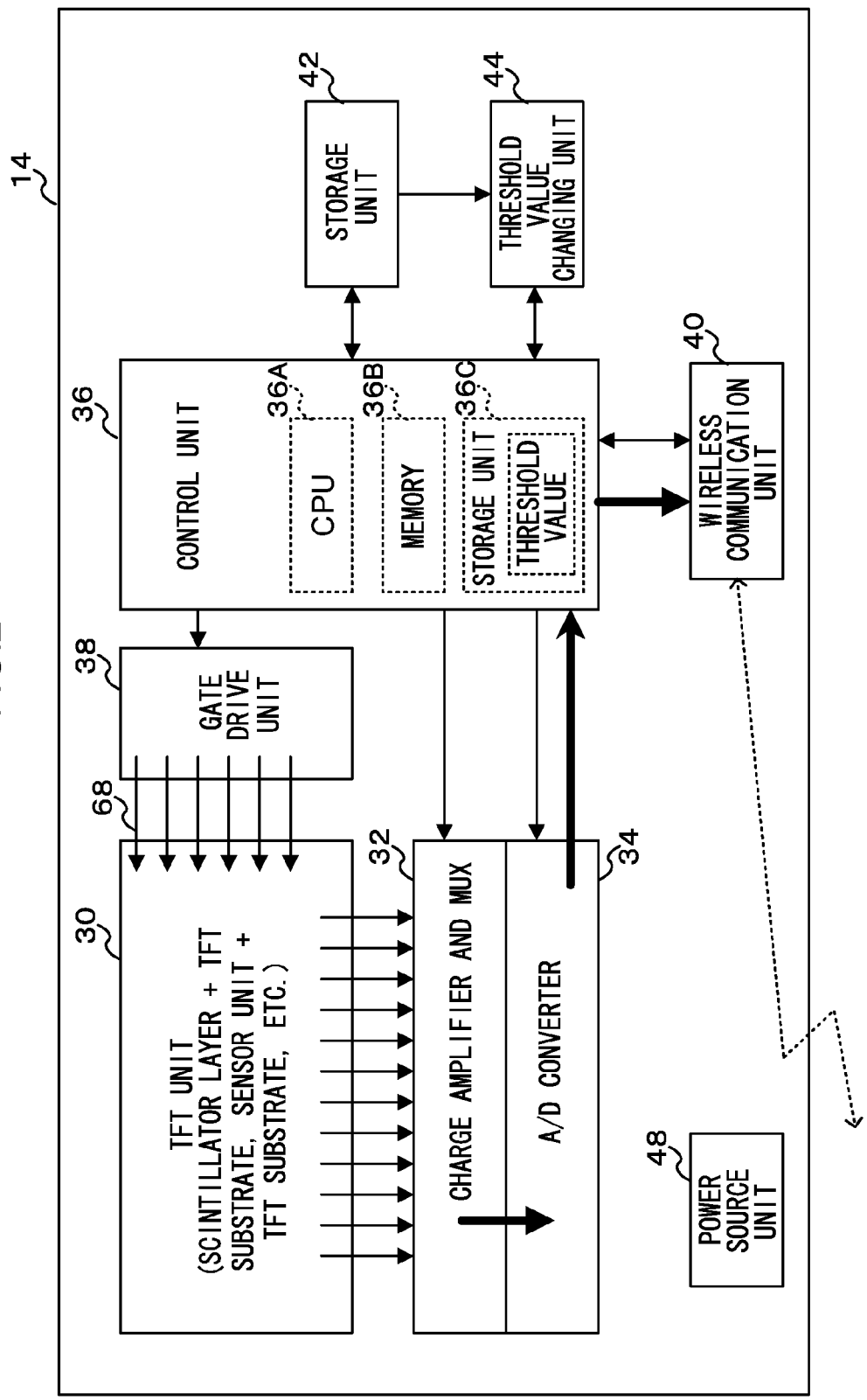
FIG. 2 is a functional block diagram showing an example of the schematic configuration of a radiation detector pertaining to the exemplary embodiment.

FIG. 2 is a functional block diagram showing an example of the configuration of the radiation detector 14. The radiation detector 14 is a radiation detection panel unit, and examples thereof include flat panel detectors (FPD) and what are known as cassettes.

The radiation detector 14 is equipped with a thin-film transistor (TFT) unit 30, a charge amplifier/multiplexer (MUX) 32, an analog-to-digital (A/D) converter 34, a control unit 36, a gate driver 38, a wireless communication unit 40, a storage unit 42, an image analyzing unit 44, and a power source unit 48.

Figure 3:
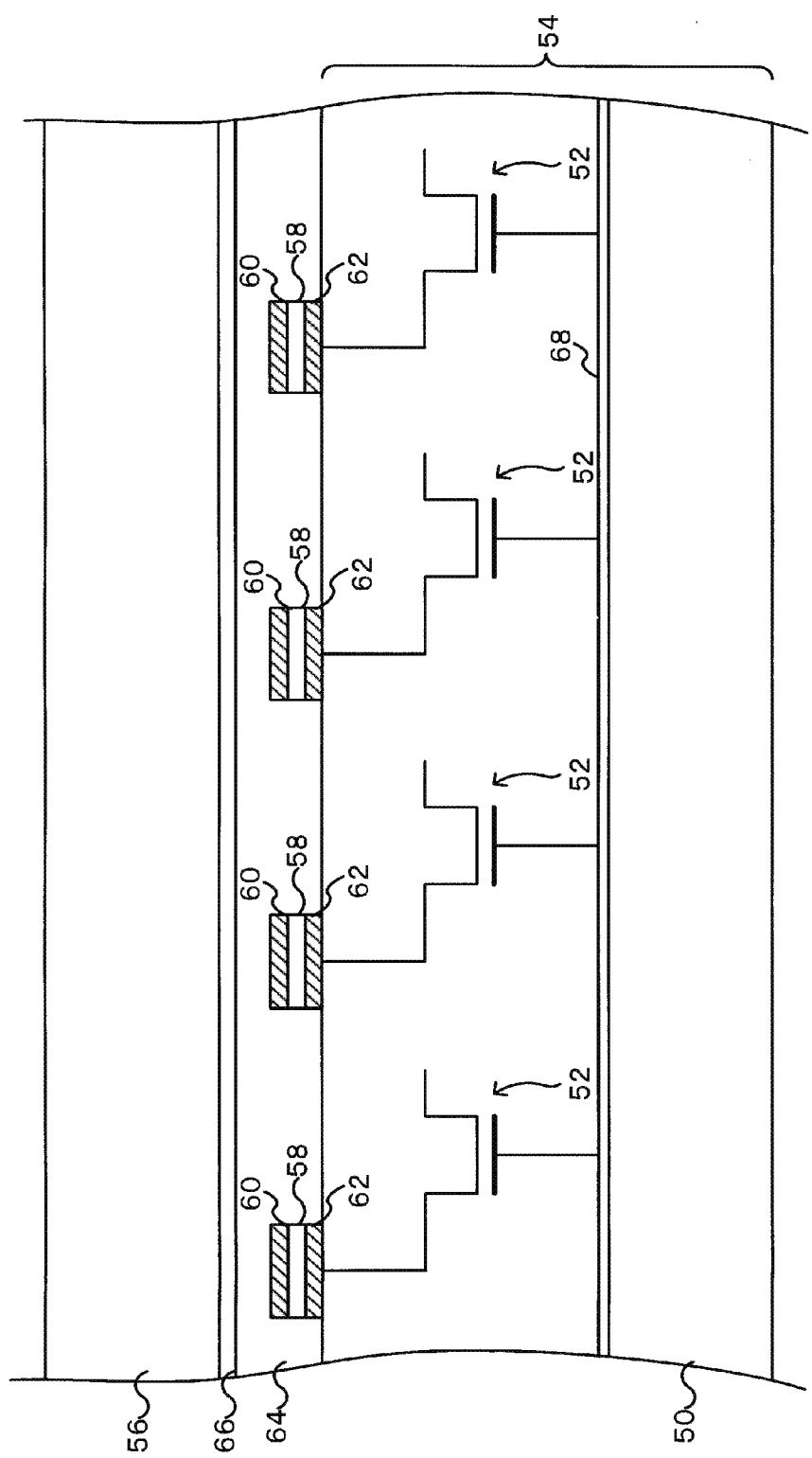
FIG. 3 is a cross-sectional view schematically showing an example of the configuration of a TFT unit of the radiation detector pertaining to the exemplary embodiment.

The TFT unit 30 detects the applied radiation. FIG. 3 is a cross-sectional view schematically showing an example of the configuration of the TFT unit 30. As shown in FIG. 3, the TFT unit 30 includes a TFT substrate 54 in which switch elements 52 such as TFTs are formed on an insulating substrate 50.

The switch elements 52 are connected to gate lines 68 for switching on and off the switch elements 52. A scintillator layer 56 that converts the radiation made incident thereon into light is formed on the TFT substrate 54. As the scintillator layer 56, for example, a CsI:Tl or GOS ($Gd_2O_2S$:Tb) phosphor or the like can be used. However, the scintillator layer 56 is not limited to these materials.

As the insulating substrate 50, for example, a glass substrate, various types of ceramic substrates, a resin substrate, or the like can be used, but the insulating substrate 50 is not limited to these materials.

Photoconductive layers 58 are placed between the scintillator layer 56 and the TFT substrate 54. The photoconductive layers 58 generates charges when the light into which the radiation has been converted by the scintillator layer 56 is made incident thereon. Bias electrodes 60 for applying a bias voltage to the photoconductive layers 58 are disposed on the surfaces of the photoconductive layers 58 on the scintillator layer 56 side.

Charge collecting electrodes 62 for collecting the charges generated by the photoconductive layers 58 are disposed on the TFT substrate 54. In the TFT substrate 54, the charges collected by the charge collecting electrodes 62 are read out by the switch elements 52.

The charge collecting electrodes 62 are arranged in a matrix (two-dimensionally) on the TFT substrate 54. In correspondence to this, the switch elements 52 are arranged in a matrix on the insulating substrate 50. A planarizing layer 64 for planarizing the top surface of the TFT substrate 54 is formed on the TFT substrate 54. Between the TFT substrate 54 and the scintillator layer 56, an adhesive layer 66 for adhering the scintillator layer 56 to the TFT substrate 54 is formed on the planarizing layer 64.

The radiation may be applied to the radiation detector 14 from the front side on which the scintillator layer 56 is adhered (i.e., the front side is the imaging surface) or may be applied to the radiation detector 14 from the TFT substrate 54 side (back side) (i.e., the back side is the imaging surface). In the case in which the radiation is applied to the radiation detector 14 from the front side, light emission at the upper surface side (the opposite side of the TFT substrate 54 side) of the scintillator layer 56 is relatively strong. In the case in which the radiation is applied to the radiation detector 14 from the back side, the radiation that has passed through the TFT substrate 54 is made incident on the scintillator layer 56, and light emission at the TFT substrate 54 side of the scintillator layer 56 is relatively strong. Charges are generated in the photoconductive layers 58 by the light that has been applied thereto by the scintillator layer 56. Therefore, the sensitivity of the radiation detector 14 with respect to the radiation can be set higher in the case in which the radiation is applied from the front side than in the case in which the radiation is applied from the back side, because the radiation does not pass through the TFT substrate 54 in the case in which the radiation is applied from the front side. In contrast, the resolution of the radiographic image obtained by the imaging is higher in the case in which the radiation is applied from the back side than in the case where the radiation is applied from the front side, because the light emission position of the scintillator layer 56 with respect to the photoconductive layers 58 is closer in the case in which the radiation is applied from the back side.

Figure 4:
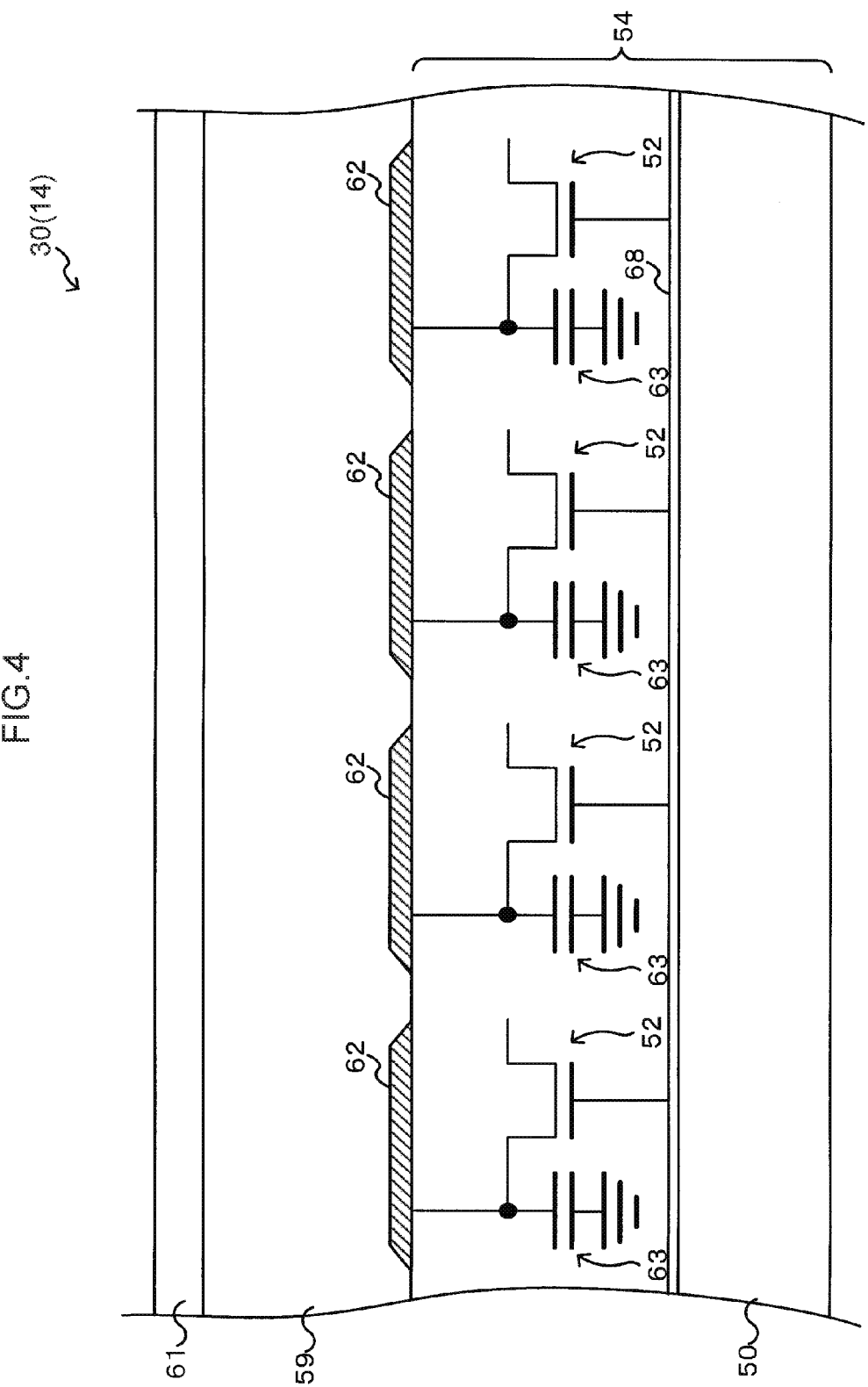
FIG. 4 is a cross-sectional view schematically showing another example of the configuration of the TFT unit of the radiation detector pertaining to the exemplary embodiment.

The structure and so forth of the TFT unit 30 is not limited to this. The TFT unit 30 may also take another structure as long as it has the function of storing and outputting charges corresponding to the radiation that has been applied to the radiation detector 14. FIG. 4 shows an example of another structure of the TFT unit 30. FIG. 4 is a cross-sectional view schematically showing another example of the configuration of the TFT unit 30. The TFT unit 30 shown in FIG. 4 employs a direct conversion structure that directly converts radiation into charges with a sensor unit using amorphous selenium or the like and stores the charges.

In the TFT unit 30 shown in FIG. 4, as an example of a radiation conversion layer that converts the radiation made incident thereon, a photoconductive layer 59 that converts the radiation made incident thereon into charges is formed on the TFT substrate 54. As the photoconductive layer 59, a compound having, as main component, at least one of: amorphous selenium (a-Se), $Bi_{12}MO_{20}$ (M: Ti, Si, Ge), $Bi_4M_3O_{12}$ (M: Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs, etc., can be used. Among them, an amorphous material is preferred which has high dark resistance, exhibits excellent photoconductivity with respect to radiation application, and is capable of being formed in a layer in a large area at a low temperature by vacuum deposition.

A bias electrode 61 is formed on the front surface of the photoconductive layer 59, which is for applying a bias voltage to the photoconductive layer 59.

In the direct conversion TFT unit 30, as in the indirect conversion TFT unit 30 (see FIG. 3), the charge collecting electrodes 62 that collect the charges generated by the photoconductive layer 59 are formed on the TFT substrate 54.

The TFT substrate 54 in the direct conversion TFT unit 30 is equipped with charge storage capacitors 63 that store the charges collected by the charge collecting electrodes 62. The charges stored in the charge storage capacitors 63 are read out by the switch elements 52. Below, there will be cases where information relating to the charges (charge information) that have been read out from the TFT unit 30 is called a QL value.

The charges that have been read out in the TFT unit 30 are outputted to the charge amplifier/MUX 32 as electrical signals. The charge amplifier 32 amplifies the electrical signals and converts the amplified electrical signals into analog voltages in the form of electrical information (data). As a specific example, the charge amplifier 32 is configured by an amplification circuit and a sample-and-hold circuit using operational amplifiers and capacitors. The electrical signals held in the sample-and-hold circuit undergo parallel-to-serial conversion in the MUX 32 and are outputted to the A/D converter 34.

The A/D converter 34 converts the serially inputted analog voltages into digital signals that are easier to handle. The two-dimensional image data of the radiographic image converted into the digital signals by the A/D converter 34 are outputted to the control unit 36. In the present exemplary embodiment, an image memory (not shown in the drawings) is connected to the A/D converter 34, and the transmitted image data are stored in sequence in the image memory. In the present exemplary embodiment, the image memory has a storage capacity capable of storing a predetermined number of frames' worth of image data, and each time the capture of a radiographic image is performed, the image data obtained by the imaging are sequentially stored in the image memory.

The control unit 36 is configured by a microcomputer, includes a CPU 36A, a memory 36B including a ROM and a RAM, and a nonvolatile storage unit 36C formed of a flash memory or the like. The control unit 36 controls the actions of the entire radiation detector 14 by executing, with the CPU 36A, various programs stored in the memory 36B.

The control unit 36 performs control of reading the storage quantity of the charges (electrical signals) stored in the TFT unit 30 intermittently after an imaging menu is registered, determining whether or not the read charge storage quantity is equal to or greater than a threshold value stored in the storage unit 36C, and, if the charge storage quantity is equal to or greater than the threshold value, determining that the timing is an imaging timing when radiation has been applied from the radiation applicator 16, starting capture of a radiographic image of the subject 19, and acquiring image data (details described later).

The control unit 36 may determine the imaging timing by reading out the storage quantity of the charges stored in predetermined pixels or dedicated pixels, determining the timing is an imaging timing is the read value of the charges has exceeded a predetermined threshold value, and performing imaging.

Alternatively, the control unit 36 may simultaneously read out the storage quantity of the charges stored in the pixels in plural row units, determine that the timing is an imaging timing if the read value of the charges has exceeded a predetermined threshold value, and perform imaging. In this case, the control unit 36 may be configured to simultaneously read out the charge storage quantity in predetermined row intervals. In either method, it is preferred that the control unit 36 perform a reset action in which it resets the charges stored until then just before starting charge storage for capturing a radiographic image.

The control unit 36 determines on the basis of the result of an image analysis by the image analyzing unit 44 whether the radiographic image is a radiographic image that has been captured at an intended timing or a radiographic image that has been captured at an unintended timing when it is not intended to perform imaging in the radiation detector 14. If the radiographic image has been captured at an unintended timing, control unit 36 controls the wireless communication unit 40 so as to prevent output of the image data of the radiographic image to the controller 12 (details described later).

The image data of the radiographic image are further transmitted from the control unit 36 to the image analyzing unit 44. The image analyzing unit 44 performs an image analysis of the radiographic image on the basis of the image data and outputs the result of the image analysis to the control unit 36.

The image data are further transmitted from the control unit 36 to the wireless communication unit 40. The wireless communication unit 40 wirelessly transmits in packets the image data per line. In this way, the wireless communication unit 40 performs wireless communication with an external device (here, the controller 12), is adapted to a wireless LAN standard represented by IEEE (Institute of Electrical and Electronics Engineers) 802.11a/b/g/n or the like, and controls the transmission of various types of data between the radiation detector 14 and the external device by wireless communication.

Through the wireless communication unit 40, the control unit 36 can perform wireless communication with an external device that controls general operation of radiographic image capturing, such as the controller 12, and can transmit various types of data to and receive various types of data from the controller 12. When capturing a radiographic image of the subject 19, the control unit 36 registers in the storage unit 42 various types of data such as information of the subject 19 and imaging conditions (imaging menu) received via the wireless communication unit 40 from the controller 12 and performs read-out of the charges on the basis of the registered imaging menu.

In this way, the capture of a radiographic image corresponding to the applied radiation is performed in the radiation detector 14. As described above, the capturing action of a radiographic image by the radiation detector 14 is executed without receiving an instruction to capture a radiographic image from the controller 12 and without being synchronized with the application of the radiation by the radiation applicator 16.

Further, the radiation detector 14 is equipped with the power source unit 48. Each of the components described above operates on electrical power supplied from the power source unit 48. The power source unit 48 has a built-in battery (a rechargeable secondary battery) so as to not impair the portability of the radiation detector 14, and the power source unit 48 supplies the electrical power to the components from the charged battery. In FIG. 2, illustration of wires connecting the components to the power source unit 48 is omitted in order to prevent the drawing from becoming complicated.

Figure 5:
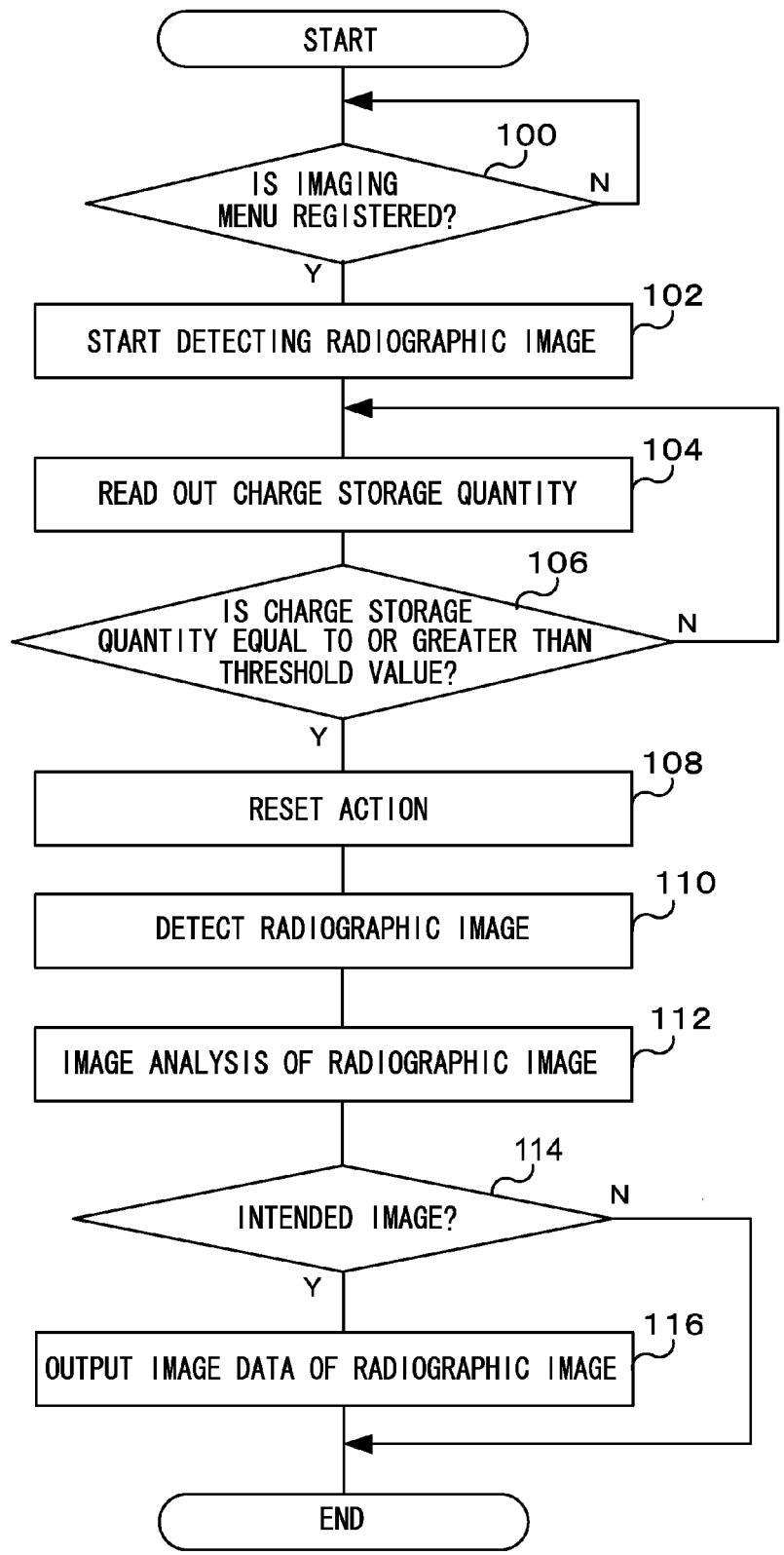
FIG. 5 is a flowchart showing an example of a flow of imaging processing that is executed in the radiation detector pertaining to the exemplary embodiment.

Next, the radiographic image capturing processing in the radiation detector 14 will be described in detail with reference to the drawings. FIG. 5 is a flowchart showing an example of a flow of radiographic image capturing processing that is executed in the radiation detector 14. When performing the imaging processing, a program stored beforehand in a predetermined area of the memory 36B is executed by the CPU 36A in the control unit 36.

In step 100, the control unit 36 determines whether or not an imaging menu has been registered. If the radiation detector 14 has not yet received an imaging menu from the controller 12, the determination in step 100 is NO and the control unit 36 stands by. If an imaging menu has been registered, the determination in step 100 is YES and the processing advances to step 102. In step 102, the control unit 36 instructs the TFT unit 30 to start detecting the radiographic image (charge information), that is, to start storing the charges.

In the next step 104, the control unit 36 reads out the charge storage quantity. In the next step 106, the control unit 36 determines whether or not the read charge storage quantity is equal to or greater than the threshold value stored in the storage unit 36C of the control unit 36. If the read charge storage quantity is less than the threshold value, the processing returns to step 104 and repeats the reading-out of the charge storage quantity and the determination of whether or not the charge storage quantity is equal to or greater than the threshold value. In contrast, if the charge storage quantity is equal to or greater than the threshold value, the determination in step 106 is YES, the control unit 36 determines that application of the radiation has been started, and the processing advances to step 108 in order to start capturing a radiographic image.

In step 108, a reset action is performed in which the charges stored in the TFT unit 30 are discharged. Thereafter, the processing advances to step 110 at which the control unit 36 detects the image data of the radiographic image in the way described above and thereby performs radiographic image capture. Thus, the image data of the radiographic image are acquired.

In the next step 112, the image analyzing unit 44 performs an image analysis of the radiographic image that has been captured. The image analyzing unit 44 performs a predetermined image analysis with respect to the radiographic image. In the present exemplary embodiment, the image analyzing unit 44 calculates a mean value of pixel values of plural pixels of the radiographic image. The plural pixels used in the image analysis may be all pixels of the radiographic image or may also, for example, be plural pixels in a predetermined region such as a head region or a center region.

The method of the image analysis is not limited to this. For example, a mean value of pixel values of plural pixels of a radiographic image in which the subject 19 has been captured (a mean value of a correct radiographic image) may be acquired beforehand and stored in the storage unit 42, and the image analyzing unit 44 may be configured to find the difference between the mean value of the pixel values of the plural pixels of the radiographic image calculated in the way described above and the mean value of pixel values of plural pixels of the correct radiographic image.

Further, a histogram of a radiographic image in which the subject 19 has been captured (a histogram of a correct radiographic image) may also be obtained beforehand, and the image analyzing unit 44 may be configured to analyze the deviation between the histogram of the radiographic image that has been captured and the histogram of the correct radiographic image.

As described above, in a case in which the radiation detector 14 misjudges that radiation has been applied and captures a radiographic image due to the radiation detector 14 being dropped or applied a shock, a radiographic image that is obtained as a result is clearly different from a correct (intended) radiographic image. For example, because the radiation detector has performed imaging in a state in which no radiation is being applied and the charge storage quantity is small, an image similar to a radiographic image of an offset image captured by the radiation detector may be obtained, or a radiographic image captured in a state in which charges have been stored only for a while immediately after the radiation detector has applied the shock may be obtained. Because the resultant image will be clearly different from a correct radiographic image, even without performing a histogram analysis, whether or not the radiographic image is an unintended image can be appropriately determined using the mean value of pixel values of plural pixels of the radiographic image. It is preferable to employ for the image analysis a method using the mean value of pixel values of plural pixels of the radiographic image because the amount of processing time can be shortened.

In the next step 114, the control unit 36 determines based on the result of the image analysis by the image analyzing unit 44 whether the radiographic image is an intended image that has been captured at an intended timing or an unintended image that has been captured at an unintended timing. Examples of methods by which the control unit 36 determines whether or not the radiographic image is an intended image based on the result of the image analysis may include a method in which mean values of plural pixels of unintended images are obtained beforehand, a range of mean values regarded as an unintended image is stored in the storage unit 42, and the control unit 36 determines whether or not the radiographic image is an intended image by whether or not the mean value of the plural pixels of the radiographic image that has been obtained as a result of the image analysis in the image analyzing unit 44 is within the range. Another example is a method in which a range of differences between mean values of plural pixels of radiographic images serving as references of wrong (unintended) images and mean values of correct (intended) radiographic images is obtained beforehand, the range of differences is stored in the storage unit 42, and the control unit 36 determines whether or not the radiographic image is an intended image by whether or not the difference of the mean value that has been obtained as a result of the image analysis in the image analyzing unit 44 is within the range. Yet another example is a method in which the control unit 36 determines whether or not the radiographic image is a correct image by a deviation with the histogram of a correct (intended) image. The method used for the determination by the control unit 36 can be determined in accordance with the image analyzing method of the image analyzing unit 44.

In a case in which the radiographic image is an intended image, the determination in step 114 is YES, and the control unit 36 advances to step 116 at which the image data of the radiographic image is output to the controller 12 via the wireless communication unit 40. Thereafter, the processing ends. In contrast, in a case in which the radiographic image is not an intended image, the determination in step 114 is NO, and the processing ends without outputting the image data of the radiographic image to the controller 12. The methods for preventing output of the subject image data to the controller 12 may include transmitting the image data of the radiographic image to the wireless communication unit 40 only if the control unit 36 has determined that the radiographic image is an intended image, or transmitting the image data of the radiographic image to the wireless communication unit 40 regardless of whether or not the radiographic image is an intended image and, if the radiographic image is an unintended image, instructing by the control unit 36 the wireless communication unit 40 not to output the image data of the transmitted radiographic image.

The image data of a radiographic image that has been determined as being an unintended image may be disposed of or may be stored in the storage unit 42 together with an indication that the image is an unintended image. In a case in which the subject image data have been disposed of, only an indication of the fact that an unintended image has been captured may be stored in the storage unit 42.

In the present exemplary embodiment, the wireless communication unit 40 does not output anything with respect to the controller 12 in a case in which the control unit 36 has determined that the radiographic image is a wrong image. However, embodiments are not limited to this and the wireless communication unit 40 may be configured to output to the controller 12 an indication that an unintended image has been captured.

As described above, the radiation detector 14 of the radiographic image capturing system 10 determines that radiation has been applied without synchronizing with the radiation application action of the radiation applicator 16. When an imaging menu is registered from the controller 12, the control unit 36 reads out the charge storage quantity of the pixels of the TFT unit 30. If the charge storage quantity that the control unit 36 has read out is equal to or greater than the threshold value stored in the storage unit 36C, the control unit 36 determined that radiation has been applied and performs radiographic image capture. The image analyzing unit 44 analyzes the captured radiographic image, and the control unit 36 determines based on the result of the image analysis whether the radiographic image is an intended image that has been captured at an intended timing or an unintended image that has been captured at an unintended timing when it is not supposed to perform imaging. Moreover, if the control unit 36 has determined that the radiographic image is an unintended image, the control unit 36 controls the wireless communication unit 40 so as to prevent transmission of the image data of the unintended image to the controller 12.

Consequently, the image capturing system 10 (radiation detector 14) can determine whether or not the radiographic image that has been captured is an image that has been detected at an intended timing.

In this way, the radiation detector 14 determined whether or not the radiographic image is an image that has been detected at an intended timing even if the radiation detector 14 has captured a radiographic image at an unintended timing such as, for example, when the radiation detector 14 has misjudged that radiation has been applied due to being dropped or applied a shock and captured a radiographic image. If the radiographic image is a radiographic image that has been detected at an unintended timing, prevents the image data from being outputted to the outside, and therefore, unnecessary image transmission does not occur because the image data are not transmitted to the controller 12. Further, in this way, because an unintended image is not transmitted to the controller 12, the imaging does not being regarded as having ended (the imaging menu does not being regarded as having been completed), and re-registration of the imaging menu for retaking will be unnecessary.

Further, the image analyzing unit 44 performs the image analysis using the mean value of plural pixels of the radiographic image, whereby processing time can be shortened compared to a case in which a histogram analysis or the like is performed.

Figure 6:
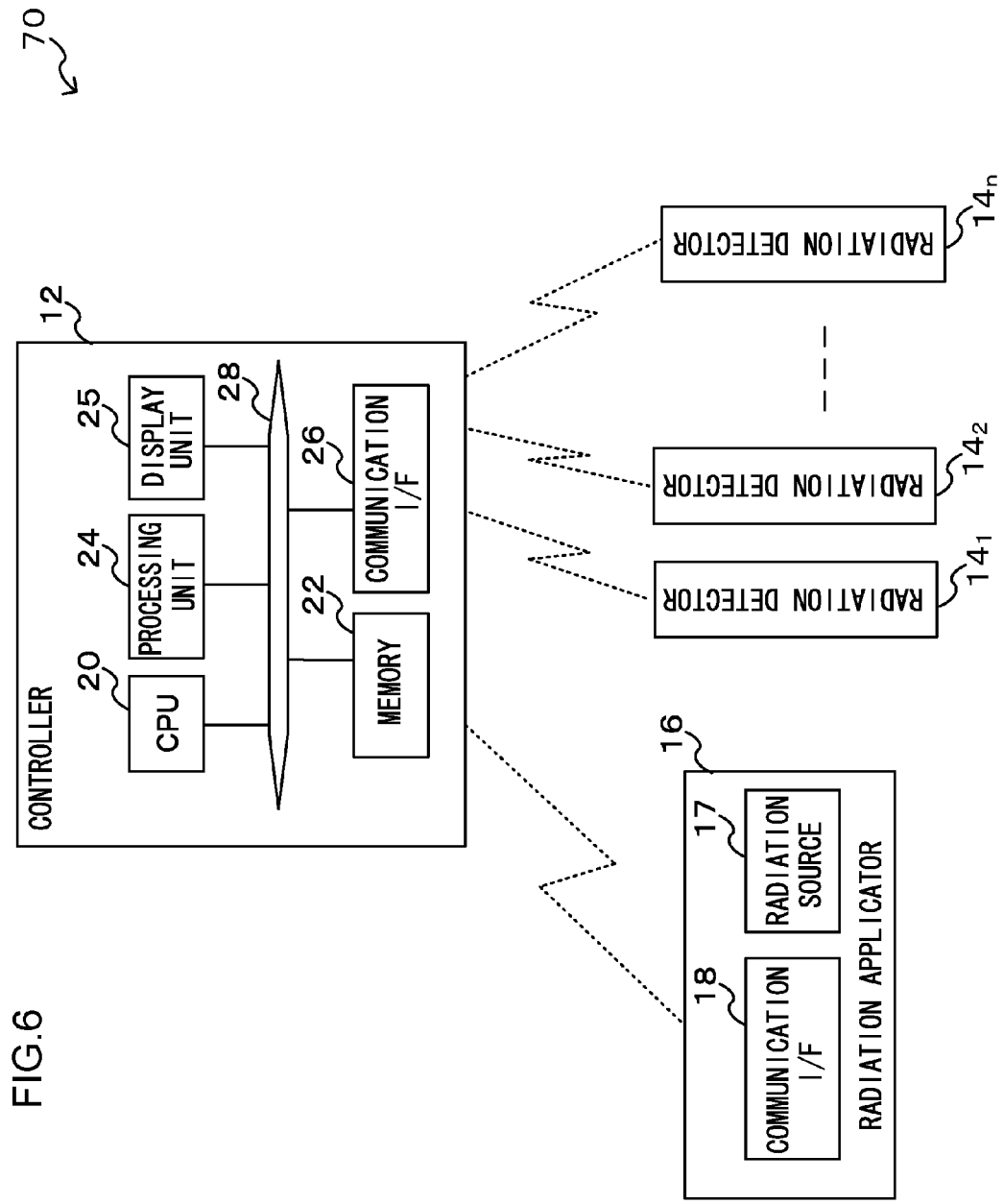
FIG. 6 is a schematic configuration diagram showing another example of the schematic configuration of the radiographic image capturing system pertaining to the exemplary embodiment and shows a radiographic image capturing system equipped with plural radiation detectors.

In the present exemplary embodiment, the radiographic image capturing system 10 equipped with one radiation detector 14 has been described, but the radiographic image capturing system is not limited to this and may also, as shown in FIG. 6, be a radiographic image capturing system 70 equipped with plural (n number in FIG. 6) radiation detectors 14.

In the radiographic image capturing system 70 equipped with the plural radiation detectors 14, for example, in a case in which only one radiation detector 14 of the plural radiation detectors $14_1$ is to capture a radiographic image, the radiation may be applied also to another radiation detector $14_2$ installed near the radiation detector 14 that is to perform imaging. The radiation detector $14_2$ that has detected the radiation performs radiographic image capture and acquires an unintended image regardless of the fact that the timing is originally not the timing when the radiation detector 14 is to perform imaging. Even in such cases, the radiation detector 14 ($14_2$) can determine based on the image analysis of the radiographic image whether the radiographic image is an unintended image or an intended image, and if it is determined that the radiographic image is an unintended image, the radiation detector 14 can prevent outputting the image data of the unintended image to the controller 12. Therefore, a waste of transmission time can be eliminated and the processing time of the workflow from the start of radiographic image capture to until the completion of output of a correct image (reception by the controller 12 is shortened, whereby convenience improves. Further, since the controller 12 receives only an intended image, the image display speed in the controller 12 can be prevented from becoming slow.

The exemplary embodiment describes above an example in which the image analysis is performed by the image analyzing unit 44 located in the radiation detector 14. However, embodiments are not limited thereto and the image analysis may be performed by the controller 12. In this case, processing time will be relatively consumed because even the image data of an unintended image is transmitted from the radiation detector 14 to the controller 12. However, the waste of re-registering the imaging menu can be eliminated by performing a determination of whether or not the imaging has ended (the imaging menu has been completed) in accordance with a determination of whether or not the radiographic image is an unintended image or an intended image performed by an image analyzing unit in the controller 12.

If the controller 12 has determined that the imaging has not ended, the controller 12 may transmit a signal indicating this to the radiation detector 14 and the radiation detector 14 may prepare to perform imaging again in the same conditions, or the same imaging menu may be again registered with respect to the radiation detector 14 from the controller 12 as if it were a new order. However, in order to eliminate the waste of re-registering the imaging menu, it is preferable that the radiation detector 14 is configured to perform imaging again in the same conditions.

The configurations and so forth of the radiographic image capturing system 10, the controller 12, the radiation detector 14, the radiation applicator 16, and so forth described in the present exemplary embodiment are examples and are capable of being changed depending on the situation without departing from the gist of the present invention.

Further, the example of the flow of the imaging processing described in the present exemplary embodiment (FIG. 5) is also an example and is capable of being changed depending on the situation without departing from the gist of the present invention.

Further, in the exemplary embodiments, cases in which X-rays are applied as the radiation have been described, but embodiments are not limited to this, and other type of radiation such as gamma rays or the like can be also used.

What is claimed is:

1. A radiation detector comprising:
a detection unit that detects image data of a radiographic image by a plurality of pixels that convert applied radiation into electrical signals and store the electrical signals;
a detection control unit that controls the detection unit so as to determine that radiation has been applied if a read value obtained by reading the electric signals stored in the plurality of pixels is equal to or greater than a threshold value and acquire image data of a radiographic image corresponding to radiation that has passed through a subject;
an image analyzing unit that performs an image analysis with respect to the radiographic image based on the detected image data if the read value is equal to or greater than the threshold value; and
a determination unit that determines on the basis of the result of the image analysis whether or not the radiographic image is an image that has been detected at an intended timing.

2. The radiation detector according to claim 1, further comprising:
an output unit that outputs the image data to the outside; and
an output control unit that controls the output unit so as to prevent outputting of the image data to the outside if the determination unit has determined that the radiographic image is not an image that has been detected at an intended timing.

3. The radiation detector according to claim 1, wherein the image analyzing unit performs the image analysis using a mean value of pixel values of a predetermined number of pixels of the radiographic image.

4. The radiation detector according to claim 1, wherein the image analyzing unit performs the image analysis on the basis of a difference between a mean value of pixel values of a predetermined number of pixels of the radiographic image and a mean value of pixel values of a predetermined number of pixels of a radiographic image that has been detected at an intended timing.

5. The radiation detector according to claim 3, wherein the predetermined number of pixels are all pixels of the radiographic image or pixels in a predetermined region of the radiographic image.

6. The radiation detector according to claim 1, wherein the detection control unit controls the detection unit in a case in which imaging conditions of a radiographic image of the subject have been registered from the outside.

7. A radiographic image capturing system comprising:
a controller that instructs imaging conditions relating to capturing a radiographic image;
a radiation applicator that applies radiation on the basis of an instruction from the controller; and
the radiation detector according to claim 1, which detects image data of a radiographic image corresponding to the radiation that has been applied from the radiation applicator and outputs the image data to the controller.

8. A radiation detection method comprising:
reading, with a detection unit that detects image data of a radiographic image by a plurality of pixels that convert applied radiation into electrical signals and store the electrical signals, the electrical signals stored in the plurality of pixels;
determining that radiation has been applied if a read value obtained by the reading is equal to or greater than a threshold value and controlling the detection unit so as to acquire image data of a radiographic image corresponding to radiation that has passed through a subject;
performing an image analysis with respect to the radiographic image based on the detected image data if the read value is equal to or greater than the threshold value; and
determining on the basis of the result of the image analysis whether or not the radiographic image is an image that has been detected at an intended timing.

9. The radiation detection method according to claim 8, further comprising preventing outputting of the image data to the outside if it has been determined that the radiographic image is not an image that has been detected at an intended timing.

10. The radiation detection method according to claim 8, wherein the image analysis is performed using a mean value of pixel values of a predetermined number of pixels of the radiographic image.

11. The radiation detection method according to claim 8, wherein the image analysis is performed on the basis of a difference between a mean value of pixel values of a predetermined number of pixels of the radiographic image and a mean value of pixel values of a predetermined number of pixels of a radiographic image that has been detected at an intended timing.

12. The radiation detection method according to claim 10, wherein the predetermined number of pixels are all pixels of the radiographic image or pixels in a predetermined region of the radiographic image.

13. The radiation detection method according to claim 8, wherein the control of the detection unit is performed in a case in which imaging conditions of a radiographic image of the subject have been registered from the outside.

14. A non-transitory storage medium storing a program causing a computer to execute radiation detection processing, the radiation detection processing comprising:
   reading, with a detection unit that detects image data of a radiographic image by a plurality of pixels that convert applied radiation into electrical signals and store the electrical signals, the electrical signals stored in the plurality of pixels;
   determining that radiation has been applied if a read value obtained by the reading is equal to or greater than a threshold value and controlling the detection unit so as to acquire image data of a radiographic image corresponding to radiation that has passed through a subject;
   performing an image analysis with respect to the radiographic image based on the detected image data if the read value is equal to or greater than the threshold value; and
   determining on the basis of the result of the image analysis whether or not the radiographic image is an image that has been detected at an intended timing.

15. A controller comprising:
   a receiving unit that receives image data that have been outputted from a radiation detector that reads electric signals from a plurality of pixels that convert applied radiation into electrical signals and store the electrical signals, determines that radiation has been applied if a read value of the electrical signals is equal to or greater than a threshold value, and detects image data;
   an image analyzing unit that performs an image analysis with respect to the radiographic image based on the received image data; and
   a determination unit that determines on the basis of the result of the image analysis whether or not the radiographic image is an image that has been detected at an intended timing.

* * * * *